(12) United States Patent
Nielsen et al.

(10) Patent No.: US 9,314,573 B2
(45) Date of Patent: Apr. 19, 2016

(54) INJECTION DEVICE WITH MEANS FOR SIGNALLING THE TIME SINCE THE LAST INJECTION

(75) Inventors: Preben Nielsen, Holbæk (DK); Christian Peter Enggaard, Vejby (DK); Thomas D. Miller, Brønshøj (DK); Bodo von Münchow, Lyngby (DK); Klaus Thogersen, Charlottenlund (DK)

(73) Assignee: Novo Nordisk A/S, Bagsvaerd (DK)

( * ) Notice: Subject to any disclaimer, the term of this patent is extended or adjusted under 35 U.S.C. 154(b) by 907 days.

(21) Appl. No.: 11/665,484

(22) PCT Filed: Oct. 20, 2005

(86) PCT No.: PCT/EP2005/011283
§ 371 (c)(1),
(2), (4) Date: Jul. 14, 2008

(87) PCT Pub. No.: WO2006/045524
PCT Pub. Date: May 4, 2006

(65) Prior Publication Data
US 2009/0076458 A1  Mar. 19, 2009

Related U.S. Application Data

(60) Provisional application No. 60/626,582, filed on Nov. 10, 2004.

(30) Foreign Application Priority Data

Oct. 21, 2004 (EP) .................................. 04077896

(51) Int. Cl.
*A61M 5/24* (2006.01)
*A61M 5/315* (2006.01)
*A61M 5/31* (2006.01)

(52) U.S. Cl.
CPC ............. *A61M 5/24* (2013.01); *A61M 5/31525* (2013.01); *A61M 5/3155* (2013.01);
(Continued)

(58) Field of Classification Search
CPC ............ A61M 2205/50; A61M 5/172; A61M 2205/582; A61M 5/16831; A61M 1/008; A61M 5/24; A61M 5/31525; A61M 5/3155; A61M 2005/3126; A61M 2205/52; A61M 2205/581; A61M 2205/583; A61M 2205/587; A61M 2205/8212
USPC ........ 604/31, 65, 67, 120, 186, 189, 207, 246
See application file for complete search history.

(56) References Cited

U.S. PATENT DOCUMENTS 4,108,177 A   8/1978   Pistor
4,428,321 A   1/1984   Arens
(Continued)

FOREIGN PATENT DOCUMENTS

CN   1705495 A   12/2005
CN   1729028 A   2/2006
(Continued)

OTHER PUBLICATIONS

FR 2740345 English Abstract, published Oct. 26, 1995.
(Continued)

*Primary Examiner* — Emily Schmidt
*Assistant Examiner* — Lauren M Peng
(74) *Attorney, Agent, or Firm* — Wesley Nicholas

(57) ABSTRACT

The present Invention relates to an injection device capable of emitting a flashing light signal indicating the time elapsed since last ejection and/or the size of the last ejected dosage and/or a return signal indicating the operable state of the device and/or a time out signal indicating when the pen can be removed after ejecting of a dosage. The injection device comprises an electronic control circuit comprising: a sensor unit arranged to detect the occurrence of an ejection of a drug from the injection device; a timer for determining an approximate time elapsed since last ejection; a signal emitting device being able to emit a signal, the signal emitting device being controllable by the electric control circuit, so as to emit a time signal that varies with the time elapsed since last ejection.

1 Claim, 3 Drawing Sheets

Figure 1:
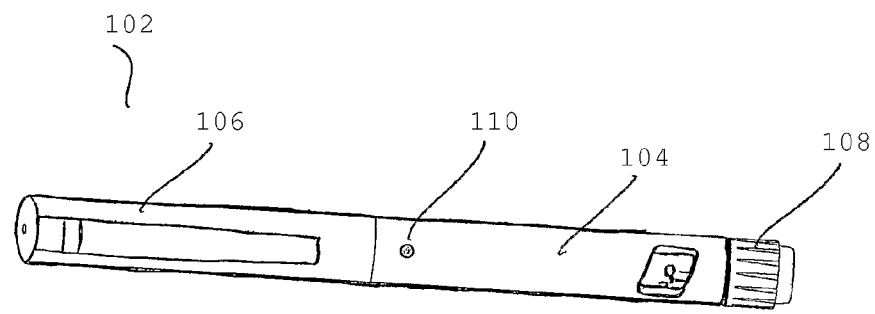

(52) U.S. Cl.
CPC ... *A61M 2005/3126* (2013.01); *A61M 2205/50* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2205/8212* (2013.01)

(56) References Cited

U.S. PATENT DOCUMENTS

| | | | |
|---|---|---|---|
| 4,515,584 | A | 5/1985 | Abe et al. |
| 4,634,431 | A | 1/1987 | Whitney et al. |
| 4,687,862 | A | 8/1987 | Obitsu et al. |
| 4,776,842 | A | 10/1988 | Franetzki et al. |
| 4,812,724 | A | 3/1989 | Langer et al. |
| 4,828,551 | A | 5/1989 | Gertler et al. |
| 4,898,578 | A | 2/1990 | Rubalcaba, Jr. |
| 5,084,021 | A | 1/1992 | Baldwin |
| 5,201,721 | A | 4/1993 | Lee et al. |
| 5,221,268 | A | 6/1993 | Barton et al. |
| 5,246,428 | A | 9/1993 | Falknor |
| 5,320,784 | A | 6/1994 | Miyashita |
| 5,324,264 | A | 6/1994 | Whitaker |
| 5,338,310 | A | 8/1994 | Lewandowski |
| 5,501,945 | A | 3/1996 | Kanakkanatt |
| 5,536,249 | A | 7/1996 | Castellano et al. |
| 5,593,390 | A | 1/1997 | Castellano et al. |
| 5,645,534 | A | 7/1997 | Chanoch |
| 5,662,612 | A | 9/1997 | Niehoff |
| 5,690,618 | A | 11/1997 | Smith et al. |
| 5,728,074 | A | 3/1998 | Castellano et al. |
| 5,755,692 | A | 5/1998 | Manicom |
| 5,998,989 | A | 12/1999 | Lohberg |
| 6,027,491 | A | 2/2000 | Hiejima et al. |
| 6,090,070 | A | 7/2000 | Hager et al. |
| 6,126,642 | A | 10/2000 | Kriesel et al. |
| 6,236,624 | B1 | 5/2001 | Kriesel et al. |
| 6,248,090 | B1* | 6/2001 | Jensen et al. ............... 604/67 |
| 6,261,469 | B1 | 7/2001 | Zakhidov et al. |
| 6,389,636 | B1 | 5/2002 | Savill |
| 6,464,663 | B1 | 10/2002 | Zinger |
| 6,620,133 | B1* | 9/2003 | Steck ............... A61M 5/20 604/131 |
| 7,008,399 | B2 | 3/2006 | Larsen et al. |
| 7,105,715 | B2 | 9/2006 | Carlucci et al. |
| 7,139,226 | B2 | 11/2006 | Haas et al. |
| 7,244,252 | B2 | 7/2007 | Berndt |
| 7,294,379 | B2 | 11/2007 | Ko et al. |
| 7,427,275 | B2 | 9/2008 | DeRuntz et al. |
| 7,785,299 | B2 | 8/2010 | Crawford et al. |
| 7,963,692 | B2 | 6/2011 | Lynn |
| 8,556,847 | B2 | 10/2013 | Kohlbrenner et al. |
| 2003/0114800 | A1* | 6/2003 | Veasey ............... A61M 5/31525 604/245 |
| 2004/0138527 | A1* | 7/2004 | Bonner ............... A61B 18/1485 600/114 |
| 2005/0222539 | A1 | 10/2005 | Gonzales et al. |
| 2006/0235086 | A1 | 10/2006 | Maskaly et al. |
| 2007/0106210 | A1 | 5/2007 | Fischer |
| 2007/0172951 | A1 | 7/2007 | Levy et al. |
| 2007/0259286 | A1 | 11/2007 | Leroux |
| 2007/0293822 | A1 | 12/2007 | Crawford et al. |
| 2008/0074643 | A1 | 3/2008 | Chen et al. |
| 2012/0103329 | A1 | 5/2012 | Smith |

FOREIGN PATENT DOCUMENTS

| | | |
|---|---|---|
| DE | 10021313 | 11/2001 |
| DE | 10201875 C1 | 5/2003 |
| DE | 102 36 669 A1 | 2/2004 |
| EP | 0 362 484 | 4/1990 |
| EP | 387854 | 9/1990 |
| EP | 688572 | 12/1995 |
| EP | 40778961 | 6/1997 |
| EP | 1074273 | 2/2001 |
| EP | 1095668 | 5/2001 |
| EP | 1804864 | 8/2008 |
| EP | 1467785 | 10/2008 |
| FR | 2740345 | 4/1997 |
| JP | 04004393 A | 1/1992 |
| JP | H0810326 A | 1/1996 |
| JP | 11134581 A | 5/1999 |
| JP | 2000-506030 | 5/2000 |
| JP | 2001-517496 | 10/2001 |
| JP | 2002-504397 A | 2/2002 |
| JP | 2005-511252 A | 4/2005 |
| JP | 2005270579 | 10/2005 |
| RU | 2140794 C1 | 11/1999 |
| SU | 1528330 A3 | 12/1989 |
| WO | WO 90/09202 | 8/1990 |
| WO | 96/04593 | 2/1996 |
| WO | WO 97/30742 | 8/1997 |
| WO | 9733638 | 9/1997 |
| WO | WO 99/15214 | 4/1999 |
| WO | 99/43283 | 9/1999 |
| WO | 00/20056 A1 | 4/2000 |
| WO | 0126710 | 4/2001 |
| WO | WO 02/056822 | 7/2002 |
| WO | 02064196 | 8/2002 |
| WO | WO 03/051429 | 6/2003 |
| WO | WO 03/092575 | 11/2003 |
| WO | 2004/010231 | 1/2004 |
| WO | 2004/062717 A1 | 7/2004 |
| WO | WO 2006/045524 | 5/2006 |
| WO | 2007/134067 | 11/2007 |
| WO | 2007134066 A2 | 11/2007 |
| WO | 2008/067143 | 6/2008 |
| WO | 2010/023303 | 3/2010 |
| WO | 2010100213 A1 | 9/2010 |

OTHER PUBLICATIONS

English Abstract of JP2005-270579 Published Oct. 6, 2005.
English Abstract of DE10021313 Published Nov. 8, 2001.
English Abstract of DE10201875 Published May 22, 2003.
English Abstract of EP387854 Published Sep. 19, 1990.
Abstract From Corresponding Application for JP2000-506030 Published May 23, 2000.
Abstract From Corresponding Application for JP2001-517496 Published Oct. 9, 2001.
Kunzelman J et al. Oligo(p-phenylene vinylene)s as a "New" Class of Piezochromic Fluorophores, "Advanced Materials" Year 2008, vol. 20, pp. 119-122.

* cited by examiner

INJECTION DEVICE WITH MEANS FOR SIGNALLING THE TIME SINCE THE LAST INJECTION

CROSS-REFERENCE TO RELATED APPLICATIONS

This application is a 35 U.S.C. §371 national stage application of International Patent Application PCT/EP2005/011283 (published as WO 2006/045524), filed Oct. 20, 2005, which claimed priority of European Patent Application 04077896.1, filed Oct. 21, 2004; this application further claims priority under 35 U.S.C. §119 of U.S. Provisional Application 60/626,582, filed Nov. 10, 2004.

FIELD OF THE INVENTION

The present invention relates to an injection device comprising a signal emitting device. In particular the present invention relates to an injection device capable of emitting a flashing light signal indicating the time elapsed since last ejection.

BACKGROUND OF THE INVENTION

In diabetes management, compliance to specified insulin regimen is important, i.e. compliance to insulin injection time schedules.

For diabetes patients, the daily injections become routine, and it is been found in various end-user studies, that diabetics sometimes are in doubt whether or not an injection has been made, or even forget to make an injection. This uncertainty about last injection makes the diabetic uneasy and in worst case leads to an additional injection with the risk of hypoglycemia.

It is known in the art to provide an injection device comprising means for indicating the time elapsed since the last ejection. An example of one such injection device is known from U.S. Pat. No. 5,645,534 which discloses a medication delivery pen having an indicator that displays the time of the last injection through interaction between a cap and pen body. After injection, the cap is replaced on the pen body such that a time of day indicator on the cap is aligned with a day of the week indicator on the pen body to visually display the time of day of that injection. The pen body includes a set of visual indicia around a circumference that represent days of the week and the cap includes visual indicia that represent different times of the day e.g. AM and PM. However, one disadvantage of this technology is that the time of the last injection is represented as a specific time of the day and thus persons crossing time zones have difficulties determining the time elapsed since the last injection.

Another example is known from in the WO 97/30742, which discloses a syringe having an electronic representation of parameters such as magnitudes of the set dose and the latest injected dose, which syringe further has a stop watch, the status of which is electronically represented and is together with the electronic represented parameters reproduced in a display showing the number of hours passed since the last operation.

Further examples may be seen in WO 90/09202, U.S. Pat. No. 6,620,133, EP 0 362 484, DE 102 36 669 and U.S. Pat. No. 5,728,074.

It is an object of a preferred embodiment of the present invention to provide an injection device wherein the time elapsed since the last injection is not relative and thus not sensitive to travelling of the patient across time zones. Furthermore, it is an object of a preferred embodiment to provide a solution which is simple and small enough to be embedded in a disposable pen.

Additionally, it is an object of a preferred embodiment to provide an injection device making it easy to determine the time elapsed since the last injection in dark surroundings. Furthermore, it is an object of a preferred embodiment of the present invention to provide an injection device wherein the power consumption of the circuit signalling time elapsed since the last injection is as low as possible.

BRIEF SUMMARY OF THE INVENTION

In order to overcome the above objectives, there is provided an injection device comprising an electronic control circuit comprising: a sensor unit arranged to detect the occurrence of an ejection of a drug from the injection device; a timer for determining an approximate time elapsed since last ejection; a signal emitting device being able to emit a signal, the signal emitting device being controllable by the electric control circuit, so as to emit a time signal that varies with the time elapsed since last ejection.

One advantage of the present invention is that the time elapsed since the last ejection is emitted to the user thus making it possible to determine if it is time for a new in injection. Thanks to the emission of the time signal, the patient may even be notified of the time since last ejection in dark surroundings. In the treatment of some diseases e.g. diabetes, it is crucial that the drug is injected at the right moment, as lack of the drug e.g. insulin can have serious consequences. Thus it is vital that the user is able to determine a need for the drug even in dark surroundings. Accordingly the present invention provides an enhanced freedom of operation for the patient.

In the context of the present invention the term "injection device" shall be understood as an instrument for introducing fluids into or withdrawing them from the body. The terms "syringe device" and "medication delivery device" may be used as synonyms for an injection device in the context of the present invention.

In the context of the present invention the term "sensor" shall be understood as a device that responds to a physical stimulus such as heat, light, sound, pressure, motion, flow, and produces a corresponding electrical signal.

The injection device may be reusable or disposable. A reusable embodiment may comprise a holder for a cartridge comprising the medication to be dispensed, whereas the compartment for the drug may be integrated in the device in the case of a disposable device which could be a disposable medication pen. One advantage of a pre-filled disposable medication pen is that the user is prevented from inserting a wrong cartridge containing a wrong medicament which may potentially harm the user.

Another advantage of a disposable medication delivery pen is that it may be more compact than a reusable pen, as the battery supplying power to the electronic control unit may be smaller due to the fact that it needs only to be able to supply power for a limited period of time compared to the reusable devices. It is a further advantage that the compartment for the medicament need not to be exchangeable, and that the device may thus be designed in a more compact way than if there were to be provided means for exchanging the compartment.

The device is able to detect the time since the last ejection and it is assumed that the user has performed an injection of the medication at this time. However, should this not be the case, the device may comprise means for resetting the device such that the time since the last ejection is calculated relative to the ejection prior to the last ejection i.e. the time of the last injection.

The signal emitted may be a light signal and/or acoustic signal and/or a tactile signal. Advantageously, the signal emitted may be a combination of two or more signals such that the device may be used by both blind and deaf persons. In one embodiment, the injection device makes it possible for the user to choose the means of signaling. For example, the user may choose to have light emitted initially and then followed by an acoustically emitted signal.

If the signal is a light signal, the signal emitting device may be a Light Emitting Diode (LED) and/or a light bulb. One advantage of the LED is that its power consumption is low both compared to a light bulb. Another advantage of an LED is that it is a cheap component to use, firstly due to its low purchasing price and secondly due to it low costs of mounting. Accordingly, by applying an LED it is possible to provide a device with low power consumption. In one embodiment, there is provided a plurality of light emitting devices and thus a scale indicating the time elapsed since last injection may be provided. In another embodiment, only two light emitting devices are provided, a first LED, which indicates the time since the last injection, and a second LED, which indicates the size of the last injection. In a further embodiment, there is only provided one LED which flashes the time elapsed since the last ejection. One advantage of a device comprising only one LED is that it is less space consuming than a display. In the present context, the term display should be understood to comprise an electronic device which is adapted to create contrasts between pixels or dots in an array of a plurality of such pixels or dots.

In another embodiment, the signal emitting device comprises an acoustic transducer which plays a sound or a series of signals indicating the time elapsed since the last ejection. In one embodiment, two signals may be emitted, one indicating that it is not yet time for a new injection, and one indicating that it is time. In yet another embodiment, the signal emitting means is a tactile indication e.g. vibration. One advantage of such a tactile indication is that the user may discretely determine the time elapsed since last injection.

The electronic control circuit may comprise an integrated circuit (IC) which may be an Application Specific Integrated Circuit (ASIC) and/or an Organic Integrated Circuit. As the ASIC is specifically designed to the injection device it is less space consuming than a standard integrated circuit. Furthermore, it is possible to integrate the clock generating device, which is needed in order to determine the time since last injection, in the ASIC.

In known electronic devices in other technical fields, clock generators are normally based on crystals, as such crystals are precise. Such crystals may also be incorporated in the present device. However, in some embodiments of the present invention, the precision an RC-based clock-generation device suffices, the clock-generation being e.g. integrated in an ASIC. Generally, the preciseness of RC-solutions is +/−5 minutes per hour. Thus, over after a period of 3-6 hours, the inaccuracy is between quarter of an hour and half an hour, which is acceptable in most insulin and other drug administration.

Another advantage of an injection device which comprises one or more LEDs is that the number of electrical connections may be limited. This is desirable, as assembling costs of an electrical device depend on the number of electrical connections. In one embodiment, the signal emitting device and the electronic control circuit are electrically interconnected by only two electrical conductors.

In order to make the device even less power consuming, the signal of the time since last ejection may not be emitted unless the user has deliberately activated the device so as to emit the signal. Thus, the signal may be emitted upon activation of an appropriate means, such as a button, which may also be the button used to eject the medicament. Alternatively, the button is only used for the purpose of activating the emitting of the time elapsed since the last ejection. In another solution, the signal is emitted upon movement of a cap in relation to the body assembly, such a cap being e.g. provided to protect the needle. The signal may be emitted upon translational movement of the cap in relation to the body assembly either by removing the cap entirely or by a small translational movement of the cap. In some embodiments, the traveled translational distance determines the signal emitted. Thus, for example the time since the last ejection may be emitted when the cap is moved a first distance, and a dosage signal (see below) may be emitted when the cap is moved a second distance.

Alternatively, the signal can be emitted upon rotational movement of the cap in relation to the body assembly. Again, different signals may be emitted depending on the rotational movement of the cap. In an even further embodiment, the time elapsed since the last ejection is emitted upon translational movement of the cap, and the dosage signal is emitted upon rotational movement of the cap.

In order to make it possible for the user to determine the time since the last ejection, the emitted signal may comprise a series of signals indicating a number of time units elapsed since last injection. In one embodiment, one signal is emitted during the first hour since the last ejection. For example, an LED may flash once at regular intervals, e.g. at intervals of 10 seconds. During the second hour since last injection, the LED may flash twice at the same intervals. In another embodiment, a first signal is emitted when one hour has elapsed, and another signal is emitted when two hours have elapsed. Alternatively, no signals may be emitted during the first hour, the emission of signals commencing at the start of the second hour since last injection.

In yet a further alternative embodiment, the frequency of the signal varies with the time since the last injection. Thus, a signal with a high frequency may be emitted right after the ejection, thus indicating that a high dosage is present in the body of the patient. As time progresses, the frequency decreases. Alternatively, the frequency may increase with the time elapsed since the last ejection. In the present context, the frequency may e.g. be a frequency of waves in an acoustic signal or in a light signal, or the frequency of a tactile signal, such as the frequency of vibrations of a vibrator.

As indicated above, the injection device may not only be adapted to emit a signal indicating the time elapsed since the last ejection. The injection device can also be able to emit a return signal indicating the operable state of the device, e.g. a low battery warning. This signal may e.g. be emitted when the cap is removed, whereby a uniform signal may be emitted. In one embodiment, the duration of the return signal is 2 seconds, whereas signals with a duration of 1 second may be used to flash the time elapsed since the last ejection.

In order to make it possible for the user to determine the size of the last ejected dosage, the device may be able to emit a dosage signal indicating the size of the last ejected dosage. The dosage signal may indicate the dosage divided with 10, i.e. 7 flashed when the dosage was 70 IU.

When the medication is to be injected, it is undesirable that the user withdraws the injected needle before the drug has been injected fully. Accordingly, in order to guide the user, the injection device may be adapted to emit a time out signal indicating when the device can be removed after ejecting of a dosage. Thus, when the needle may be removed, an LED may start to flash, or an LED may be turned off when the needle may be removed. Alternatively, a sound may be played when the needle may be removed.

In order to choose a dosage, a dosage setting device may be provided at one end of the injection device, e.g. at that end which is opposite to the needle. The sensor unit may be provided in the dosage setting device, thus making it possible to determine that a button of the dosage setting device is activated when the drug is to be dispensed. Alternatively, the sensor is adapted to determine when the dosage setting device is pushed back to the initial position, at which the dosage is set to 0 IU.

In one embodiment the emitted signal is used to transfer data from the injection device to an external device. The external device may comprise a sensor which is adapted to detect the emitted signal. The signal may be any type of signal described in the aforementioned. The data may be any of type of information described in the aforementioned. In one embodiment the emitted signal comprises the entire use-history of the device.

In one embodiment the signal is in a range which is not visible to the human eye or audible to the human ear. Thus, if the signal is an audible, the signal may be below 20 Hz and/or above 20.000 Hz. If the signal is a visible signal, the signal may be below 380 nm and/or above 780 nm. The signal may be superposed a signal which is used to communicate information to the user. Thus, in one embodiment the signal emitting device emits a one signal to the user while at the same time it emits a second superposed signal to the external device. In the case of a superposed light signal the signal may be emitted at a wavelength which is within the visible spectrum, however in order to make it invisible for the user, it may be switched on and off at a high frequency such as a frequency higher than 100 Hz.

DETAILED DESCRIPTION OF THE INVENTION

Figure 2:
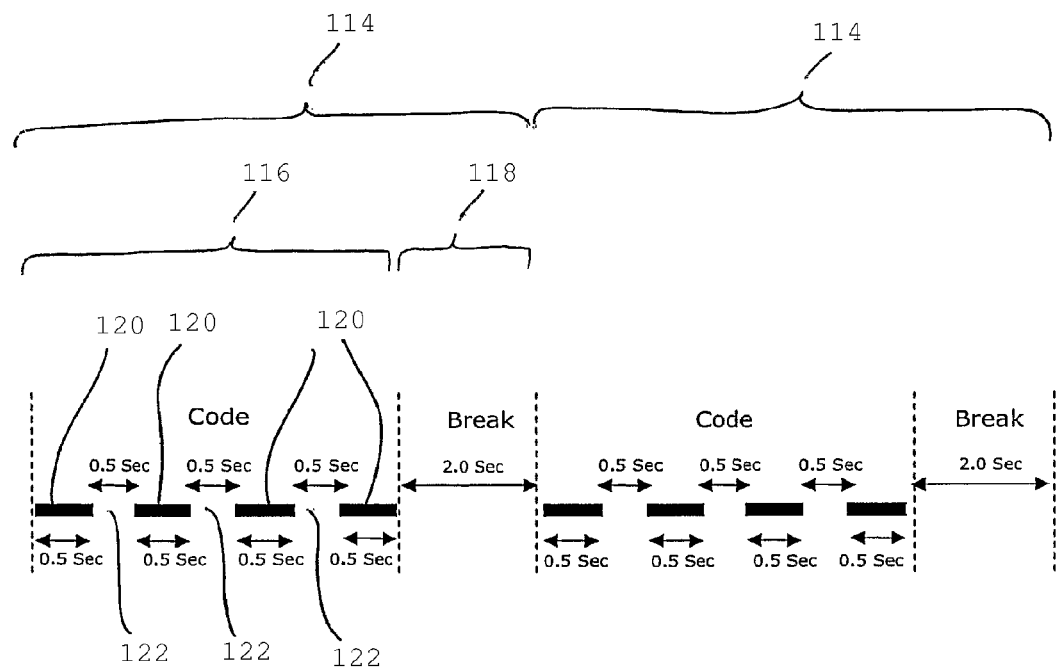
Figure 3:
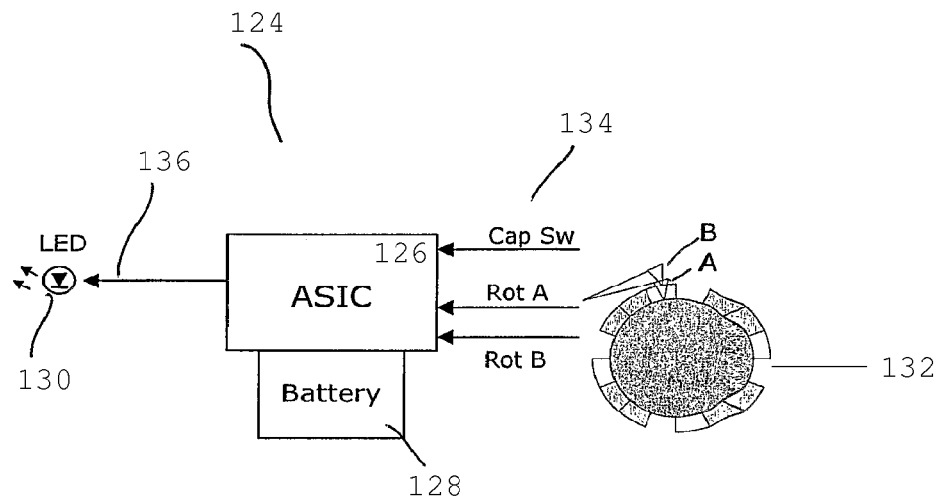
Figure 4:
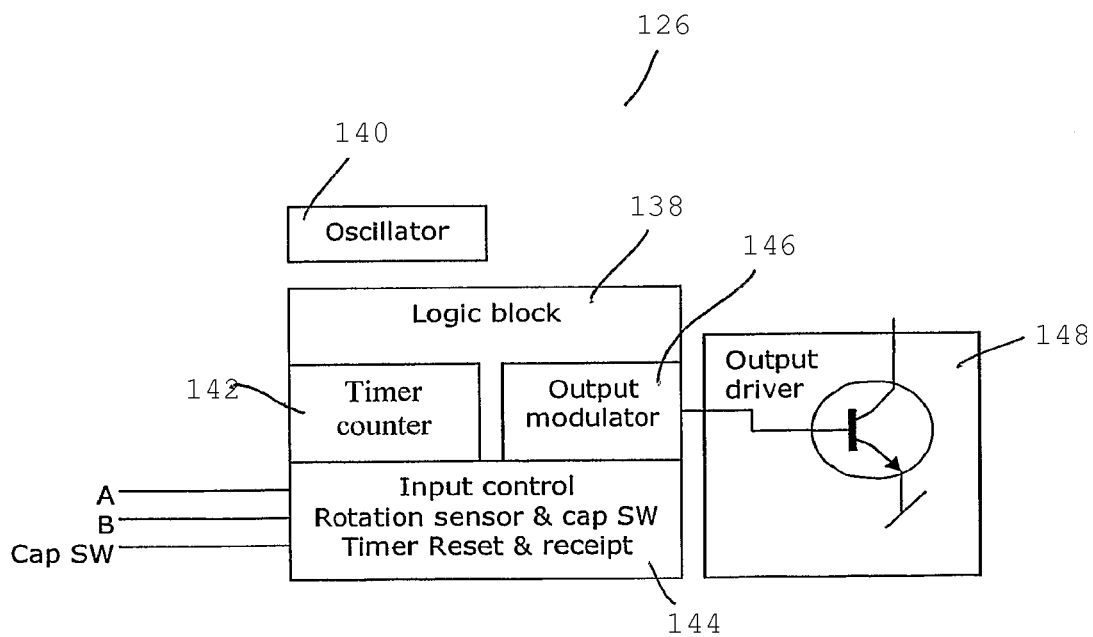
Figure 5:
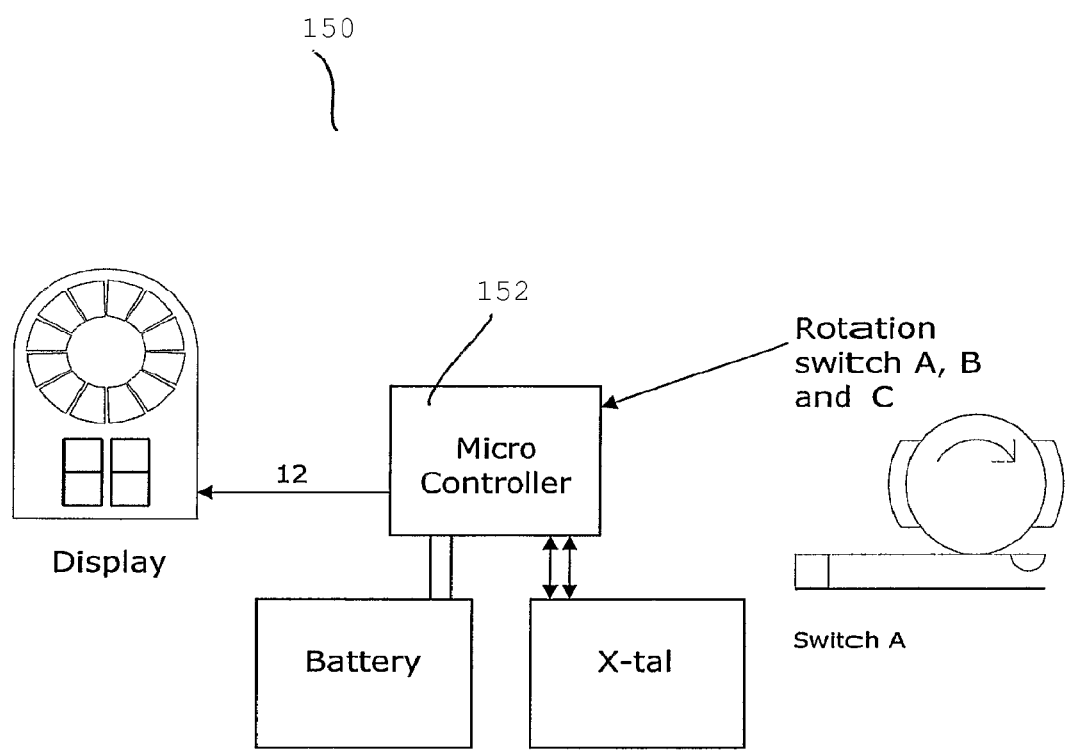

The invention will now be described in further detail with reference the drawings, in which:

FIG. 1 shows an embodiment of the injection device according to the present invention, FIG. 2 shows a signal emitting pattern of an injection device according to the present invention, FIG. 3 shows an electrical control circuit of an injection device according to the present invention, FIG. 4 shows the internal architecture of an ASIC used in the present injection device, and FIG. 5 shows a diagram of a prior art electrical control circuit.

FIG. 1 shows an injection device 102 according to the present invention. The injection device is shown as a medication delivery pen for insulin and comprises a pen body 104 and a cap 106. On the pen body 104 is provided a dose setting member 108 which may be used to set the dose to be injected. A signal emitting means 110 is provided on the pen body 104, but may alternatively be provided on the cap 106 or on a part of the pen body which is covered by the cap when said cap is attached to the pen. In the drawing, the signal emitting means is an LED.

An example of a signaling pattern of a signal emitting means of an injection device according to the present invention is disclosed in FIG. 2. The signaling pattern comprises a sequence 114 comprising a signaling phase 116 and an interruption period 118. During the signaling phase 116 a plurality of signals 120 are emitted. The duration of the signals 120 is 0.5 seconds and they are interrupted by intervals 122 also lasting 0.5 seconds. In the example, four signals 120 are emitted indicating that four hours have elapsed since the last ejection. The duration of the interruption periods 118 is 2 seconds in the example of FIG. 2.

An example of an electrical control circuit 124 of the present invention is shown in FIG. 3. The electrical control circuit 124 comprises an Application Specific Integrated Circuit 126, a battery 128, a signal emitting device 130, and a rotational switch 132 and a cap switch 134 (not shown). The ASIC 126 is interconnected to the signal emitting device 130 by means of one set of electrical conductors 136 (the ground conductor is not shown). Additionally, the battery 128 and the ASIC 126 are interconnected by one set of electrical conductors (not shown). The rotational switch 132 and the ASIC 126 are interconnected by two electrical conductors as well as by a ground conductor which is not shown in FIG. 3. The cap switch 134 is connected to the ASIC 126 by one conductor as well as by a ground conductor which is not shown. Thus, a total of nine electrical conductors are provided in the electrical control circuit 124 of FIG. 3.

The internal architecture of the ASIC 126 is shown in FIG. 4. The ASIC 126 comprises a logic block 138, which serves as an operative foundation of the ASIC. An oscillator 140 of the RC type is integrated in the ASIC. In order to count the time elapsed since the last ejection, a timer counter 142 is provided. Input to the device is controlled by an input controller 144. Output is controlled by an output modulator 146, which via an output driver 148 sends signals to the signal emitting device. In operation, the timer counter 142 counts oscillations of the oscillator 140. The input controller 144 receives signals from a rotation sensor and cap switch (cap SW) indicative of the occurrence of an injection. The rotation sensor and the cap switch determine the quantity of an injected dose as well as the occurrence of an injection. The timer counter tracks the time elapsed since the last occurrence of an injection and passes a signal indicative of that time to the output driver 148 which causes the signal emitting device, e.g. the LED of FIG. 3, to emit a signal indicative of the time elapsed since last injection.

An example of a prior art device 150 is shown in FIG. 5. The device comprises a standard microcontroller 152.

The invention claimed is:

1. An injection device (102) comprising an electronic control circuit (126,152) comprising:
    a dosage setting device for setting the dose to be injected;
    a sensor unit arranged to detect the occurrence of an ejection of a drug from the injection device, by determining that a button of the dosage setting device is activated;
    a timer (142) for determining an approximate time elapsed since completion of last ejection;
    a signal emitting device (110,130) being able to emit a signal (114), the signal emitting device (110,130) being controllable by the electric control circuit, so as to emit a time signal that varies with the time elapsed since completion of last ejection,
    wherein, the emitted time signal consists of a flashing light indicating the time elapsed since completion of last ejection, and wherein the frequency at which the flashing light flashes increases with the time elapsed since completion of last ejection.

* * * * *